(12) United States Patent
Nokuo et al.

(10) Patent No.: US 7,388,365 B2
(45) Date of Patent: Jun. 17, 2008

(54) METHOD AND SYSTEM FOR INSPECTING SPECIMEN

(75) Inventors: Takeshi Nokuo, Tokyo (JP); Satoru Kawase, Tokyo (JP); Tadaharu Mouri, Tokyo (JP)

(73) Assignee: Jeol Ltd., Tokyo (JP)

( * ) Notice: Subject to any disclaimer, the term of this patent is extended or adjusted under 35 U.S.C. 154(b) by 60 days.

(21) Appl. No.: 11/224,847

(22) Filed: Sep. 13, 2005

(65) Prior Publication Data

US 2006/0054813 A1 Mar. 16, 2006

(30) Foreign Application Priority Data

Sep. 13, 2004 (JP) ............................. 2004-265028
May 24, 2005 (JP) ............................. 2005-151157

(51) Int. Cl.
*G01R 15/00* (2006.01)
(52) U.S. Cl. ................................................. 324/158.1
(58) Field of Classification Search ..................... None
See application file for complete search history.

(56) References Cited

U.S. PATENT DOCUMENTS

| | | | | |
|---|---|---|---|---|
| 4,983,830 A * | 1/1991 | Iwasaki | .................... | 324/158.1 |
| 5,267,471 A * | 12/1993 | Abraham et al. | ............ | 250/306 |
| 5,431,055 A * | 7/1995 | Takata et al. | ................ | 250/307 |
| 5,502,306 A * | 3/1996 | Meisburger et al. | ........ | 250/310 |
| 5,821,545 A * | 10/1998 | Lindsay et al. | ........... | 250/443.1 |
| 6,185,991 B1 * | 2/2001 | Hong et al. | .................... | 73/105 |
| 6,198,300 B1 * | 3/2001 | Doezema et al. | ........... | 324/762 |
| 6,389,886 B2 * | 5/2002 | Daniels et al. | ................. | 73/105 |
| 6,552,556 B1 * | 4/2003 | Miki | ........................... | 324/754 |
| 6,930,479 B2 * | 8/2005 | Xiao et al. | .................... | 324/262 |
| 6,970,004 B2 * | 11/2005 | Ishitani et al. | ............... | 324/752 |
| 7,098,055 B2 * | 8/2006 | Noguchi et al. | ............... | 438/18 |
| 7,112,792 B2 * | 9/2006 | Agemura et al. | ........... | 324/765 |
| 7,129,727 B2 * | 10/2006 | Saito et al. | .................. | 324/754 |
| 7,187,186 B2 * | 3/2007 | Shi et al. | ..................... | 324/752 |
| 7,233,867 B2 * | 6/2007 | Pisupati et al. | ............. | 324/255 |
| 2003/0175945 A1 * | 9/2003 | Thompson et al. | ......... | 250/305 |
| 2004/0178811 A1 * | 9/2004 | Ishitani et al. | .............. | 324/751 |
| 2004/0239318 A1 * | 12/2004 | Xiao et al. | ................... | 324/529 |
| 2005/0146714 A1 * | 7/2005 | Kitamura et al. | ........ | 356/237.2 |
| 2006/0043982 A1 * | 3/2006 | Shinada et al. | ............. | 324/751 |
| 2006/0192574 A1 * | 8/2006 | Furukawa et al. | .......... | 324/750 |
| 2007/0126458 A1 * | 6/2007 | Shi et al. | ..................... | 324/765 |

FOREIGN PATENT DOCUMENTS

| | | |
|---|---|---|
| JP | 10-214584 | 8/1998 |
| JP | 2001-185593 | 7/2001 |

* cited by examiner

*Primary Examiner*—Jermele M Hollington
(74) *Attorney, Agent, or Firm*—The Webb Law Firm (57) ABSTRACT

Method and system for obtaining a potential distribution image of a specimen using two probes having two probes contacted with a patterned surface of the specimen, a scanning unit for scanning a beam of electrons or ions over the specimen, a potential detection unit for detecting the electric potential at an arbitrary position on the specimen using the probes, and an acquisition unit for obtaining a potential distribution image of the specimen while synchronizing the output from the potential detection unit with the scanning of the beam.

22 Claims, 7 Drawing Sheets

METHOD AND SYSTEM FOR INSPECTING SPECIMEN

BACKGROUND OF THE INVENTION

1. Field of the Invention

The present invention relates to a method and system for inspecting a specimen using at least one probe.

2. Description of Related Art

Known specimen inspection systems for measuring the physical properties of a specimen in a scanning electron microscope (SEM) include an inspection system using an electron beam-induced current (EBIC) method and an inspection system using an electron beam LSI tester or cathodoluminescence. Of these systems, inspection systems using cathodoluminescence measure physical properties of specimens by a technique utilizing optical physical properties. On the other hand, in inspection systems using EBIC, a lead wire or interconnect line connected with a probe in contact with a wide-area electrode (usually known as a pad) or an interconnect line bonded to the pad is brought to the outside of the SEM specimen chamber, and the EBIC is measured outside the SEM.

One conventional system of this kind has a control means for irradiating a specimen with a focused electron beam and controlling the beam position on the specimen, a secondary electron detector, plural probes each having a sharp tip, a voltage source for applying a voltage between the probes, an ammeter for measuring the electrical current flowing between the probes, and a means for storing the value of the current flowing between the probes in a corresponding manner to the beam position on the specimen (see, for example, Japanese Patent Laid-Open No. 2001-185593 (pages 4 and 5; FIG. 1)).

Another conventional system of this kind consists basically of an SEM. Two or more metallic microprobes are mounted in the SEM. The probes are operated at high accuracy to precisely detect the electrical characteristics of microscopic areas of ceramics (see, for example, Japanese Patent Laid-Open No. H10-214584 (pages 3 and 4; FIG. 1)).

A further available method is used to inspect for defects in a specimen using an electron microscope or FIB (focused ion beam) system. In this method, an electrical potential produced on the specimen when it is scanned with an electron beam or ion beam is observed as a contrast difference. This potential difference imaging method visualizes abnormal potentials caused by charge-up as variations in brightness of secondary electrons when a specimen surface is irradiated with an electron beam or ion beam.

In the prior art potential difference imaging method, the difference in secondary electron emission efficiency between positively and negatively charged portions of a specimen is recognized as an image and so it has been impossible to detect minute variations in voltage.

SUMMARY OF THE INVENTION

The present invention has been made in view of the foregoing problems. It is an object of the invention to provide a method and system for inspecting a specimen by detecting minute variations in voltage on the specimen.

A first method of inspecting a specimen in accordance with the present invention consists of bringing a probe into contact with a specimen at a given position, scanning a beam of electrons beam or ions over the specimen, and detecting a signal taken from the probe in synchronism with the scanning of the beam. Thus, a potential distribution image of the specimen is acquired.

A second method of inspecting a specimen in accordance with the present invention consists of bringing a probe into contact with a specimen at given positions, scanning a beam of electrons or ions over the specimen to induce an absorption current through the probe or a voltage on the probe, synchronizing the absorption current or voltage with the scanning of the beam, and gaining a potential distribution image of the specimen.

A third method of inspecting a specimen in accordance with the present invention consists of grounding one end of an interconnect pattern formed on the specimen, connecting a voltage detector with the other end of the interconnect pattern via a probe, scanning a beam of electrons or ions over the specimen, detecting the resulting signal by the voltage detector, synchronizing the detected signal with the scanning of the beam and gaining an image, and overlapping this image on a secondary electron image or backscattered electron image obtained by the scanning of the beam.

A fourth method of inspecting a specimen in accordance with the present invention consists of bringing first and second probes into contact with an interconnect pattern formed on the specimen at first and second positions, respectively, scanning a beam of electrons or ions, detecting a voltage produced during scanning of the beam via one of the probes, detecting an electrical current produced during the scanning via the other of the probes, and gaining the resistance value of an interconnect pattern portion on the specimen located between the probes based on the detected voltage and current.

A first specimen inspection system based on the present invention comprises a probe contacted with a surface of a probe, scanning means for scanning a beam of electrons or ions over the specimen, potential detection means for detecting an electric potential on the specimen via the probe, and image acquisition means for gaining a potential distribution image of the specimen while synchronizing an output from the potential detection means and the scanning of the beam.

A second specimen inspection system based on the present invention comprises a probe contacted with a surface of a probe, scanning means for scanning a beam of electrons or ions over the specimen, detection means for detecting an absorption current flowing through the specimen or a voltage on the specimen via the probe, and image acquisition means for gaining an image while synchronizing the detected signal and the scanning of the beam.

A third specimen inspection system based on the present invention comprises first and second probes contacted with a specimen, scanning means for scanning a beam of electrons or ions over the specimen, voltage detection means for detecting a voltage produced during the scanning of the beam via one of the probes, current detection means for detecting an electrical current produced during the scanning of the beam via the other of the probes, and resistance value acquisition means for gaining a resistance value based on the detected voltage and current.

According to the first specimen inspection method based on the present invention, a potential distribution image of the specimen can be obtained while synchronizing the signal obtained from the probe with the scanning of the beam of electrons or ions. Thus, minute variations in voltage on the specimen can be detected.

According to the second specimen inspection method based on the present invention, a potential distribution image of the specimen is obtained while synchronizing the signal of the absorption current flowing through the probe or voltage on the probe with the scanning of the beam of electrons or ions. Consequently, it is possible to detect minute variations in voltage on the specimen.

According to the third specimen inspection method based on the present invention, an image is obtained while synchronizing a voltage signal from an interconnect pattern formed on a specimen with the scanning of the beam of electrons or ions. This image is superimposed on a secondary electron image or backscattered electron image of the specimen. Thus, the position of an abnormal portion, if any, on the specimen can be identified.

According to the fourth specimen inspection method based on the present invention, a voltage produced during scanning of the beam is detected via one probe. An electrical current produced during the scanning is detected via the other probe. The resistance value of the interconnect pattern portion located between the probes on the specimen is gained based on the detected voltage and current. Therefore, the resistance value of the interconnect pattern portion can be easily detected.

According to the first specimen inspection system based on the present invention, a signal which indicates a potential on the specimen and is obtained via the probe can be synchronized with the scanning of the beam of electrons or ions, and a potential distribution image of the specimen can be obtained. Hence, minute variations in voltage on the specimen can be detected.

According to the second inspection system based on the present invention, a signal which indicates an absorption current or voltage on the specimen and is obtained via the probe is synchronized with the scanning of the beam of electrons or ions, and an image is obtained. Thus, minute variations in voltage on the specimen can be detected.

According to the third specimen inspection system based on the present invention, a voltage produced during scanning of the beam is detected via one probe. An electrical current produced during scanning of the beam is detected via the other probe. The resistance value of the interconnect pattern portion on the specimen located between the probes is measured based on the detected voltage and current. Therefore, the resistance value of the interconnect pattern portion can be easily detected.

Other objects and features of the invention will appear in the course of the description thereof, which follows.

DESCRIPTION OF THE PREFERRED EMBODIMENTS

The preferred embodiments of the present invention are hereinafter described in detail with reference to the accompanying drawings.

Figure 1:
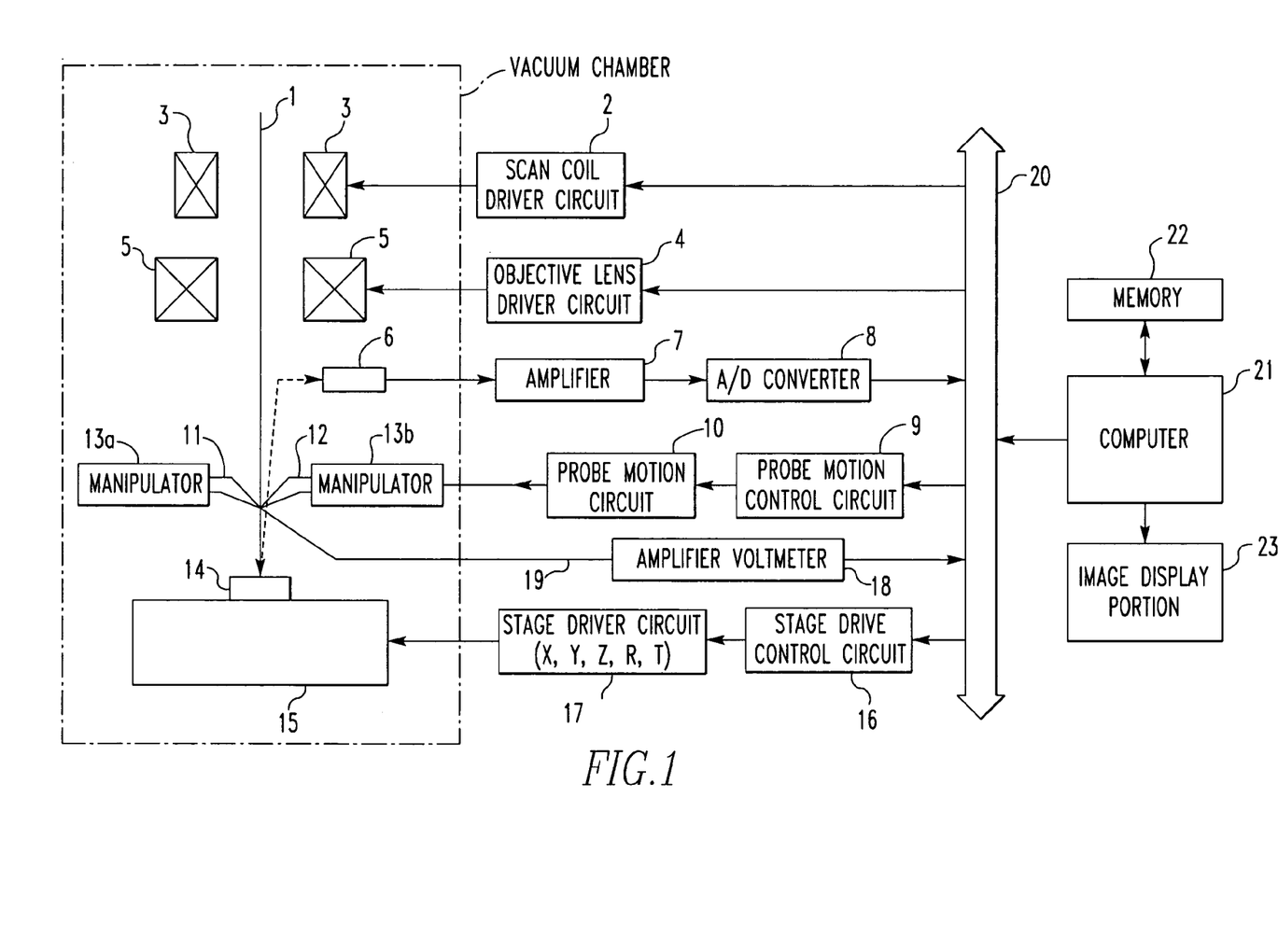
FIG. 1 is a block diagram showing a first embodiment of the present invention.

FIG. 1 is a block diagram illustrating a first embodiment of the present invention. Indicated by numeral 1 is an incident beam of electrons or ions. Scan coils 3 are driven by a scan coil driver circuit 2. An objective lens 5 is driven by an objective lens driver circuit 4.

A signal such as a secondary electron signal produced from a specimen is detected by a detector 6. The output from the detector 6 is amplified by an amplifier 7. The output from the amplifier 7 is converted into digital image data by an A/D converter 8. A probe motion control circuit 9 produces a control signal for moving probes (described in detail later). The output from the probe motion control circuit 9 is received by a probe motion circuit 10. The position of a first probe 11 is moved by the probe motion circuit 10. Indicated by numeral 12 is a second probe. Manipulators 13a and 13b drive the probes 11 and 12, respectively. For example, piezoelectric devices are used as the manipulators 13a and 13b.

The aforementioned specimen is indicated by numeral 14 and moved by a specimen stage 15. A stage drive control circuit 16 produces a control signal for moving the specimen stage 15. A stage driver circuit 17 receives the output from the stage drive control circuit 16 and drives the specimen stage 15 in X, Y, Z, R, and T directions. The voltage signal from the second probe 12 is transmitted by a coaxial cable 19. A voltage detecting amplifier-voltmeter 18 is connected with the coaxial cable 19 and amplifies a voltage signal at the given position on the specimen. The output from the amplifier-voltmeter 18 is converted into digital image data by an A/D converter (not shown) and then fed to a bus 20.

The bus 20 is connected with all of the scan coil driver circuit 2, objective lens driver circuit 4, A/D converter 8, motion control circuit 9, voltage detecting amplifier-voltmeter 18, and stage drive control circuit 16. A computer 21 forming an image acquisition means is connected with the bus 20 and controls these various components. A memory 22 is connected with the computer 21 and stores given information. An image display portion 23 is connected with the computer 21 and displays a potential distribution image of the specimen 14 and other data. A CRT or liquid crystal display is used as the image display portion 23. The operation of the system constructed as described so far is described below.

The incident beam of electrons or ions is scanned over the specimen 14 by the scan coils 3. Secondary electrons emanating from the scan point on the specimen 14 are detected by the detector 6. The output signal from the detector 6 is amplified by the amplifier 7 and then converted into digital signal data by the A/D converter 8. The output from the A/D converter 8 is fed via the bus 20 into the computer 21, where the signal is imaged. In this way, an image is obtained. This image is displayed on the image display portion 23. The computer 21 identifies portions with which the probes are contacted, based on this image.

To bring the probes into contact with the portions identified within the image, a signal is produced from the computer 21 to control the probe motion control circuit 9 via the bus 20, the control circuit 9 driving the manipulators. The probe motion circuit 10 receiving this signal drives the manipulators 13a and 13b. The probes 11 and 12 mounted at the tips of the manipulators 13a and 13b are manipulated. The probes 11 and 12 are electrically isolated from other portions and can detect voltages.

A voltage measurement is performed from the tip of the probe 12 in contact with a certain portion of the specimen 14 via the coaxial cable 19 and amplifier-voltmeter 18. At this time, the probe motion control circuit 9 and probe motion circuit 10 have a motion resolution of less than 10 nm to achieve accurate positioning within an electron microscope or ion beam system. Furthermore, to permit the probes 11 and 12 to approach the specimen 14 with ease, the probes are tilted at an angle of greater than 30 degrees. During the approach of the probes, the probes and specimen are grounded to prevent discharging; otherwise, the probes would be damaged.

The computer 21 displays information obtained via the detector 6 and amplifier 7 on the viewing screen on a real-time basis. Furthermore, the computer superimposes a secondary electron image or potential distribution image. Since a scanned image of the specimen has positional information, the position of an abnormal portion, if any, can be confirmed by superimposing the scanned image of the specimen on the potential distribution image of the specimen as described above and displaying the resultant image.

According to this embodiment, the signal obtained from the second probe 12 can be represented in gray scale on the image display portion 23 relative to the signal from the first probe 11 in synchronism with the scanning of the beam. Minute variations in a physical property of the specimen can be detected.

Figure 2:
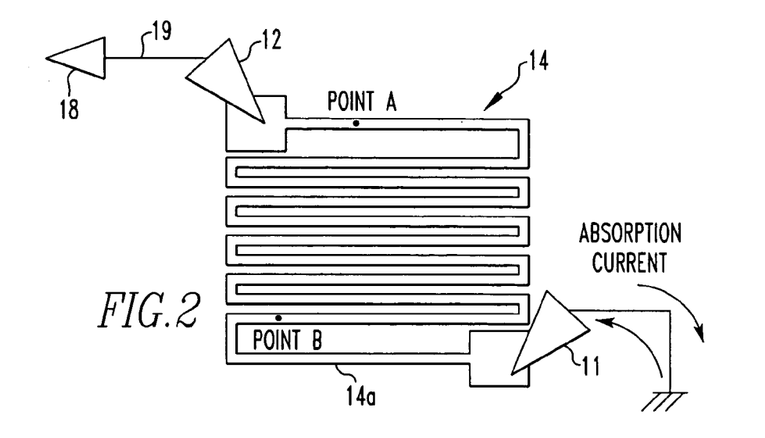
FIG. 2 is a diagram showing a first example of main portions of the present invention.

FIG. 2 shows a first example of main portions of the present invention. Like components are indicated by like reference numerals in both FIGS. 1 and 2. In FIG. 2, the first probe 11 and second probe 12 are in contact with an interconnect pattern 14a formed on the specimen 14 at given positions. The first probe 11 is grounded. The second probe 12 is in contact with the specimen 14 at a given position and held. A voltage signal taken from the second probe 12 is fed into the following voltage detecting amplifier-voltmeter 18 via the coaxial cable 19. The signal is extracted as a potential distribution image. The operation of the system constructed in this way is described below.

The two probes 11 and 12 are moved into target positions and contacted with the specimen, and then the probe 11 is grounded. The probe 12 is sequentially connected with the voltage-detecting amplifier-voltmeter 18. When the focused beam is made to hit a point B on the interconnect pattern 14a, secondary electrons are ejected from the point B. The difference between the beam current produced at this time and the electrical current induced by the generation of the secondary electrons constitutes an absorption current. This absorption current flows, for example, from the grounded point to the point B in the interconnect pattern 14a. When the beam hits a point A, an absorption current similarly flows.

Since the interconnect pattern 14a is made of the same material at this time, the secondary electron emission efficiency is uniform. Accordingly, if the beam current is constant, the amount of absorption current is uniform on every point on the interconnect pattern. Where the absorption current flowing from the grounded point to the point B is equal to the absorption current flowing from the grounded point to the point A in this way, the resistance value of the interconnect pattern portion located between the grounded point and the point B is smaller than the resistance value of the interconnect pattern portion located between the grounded point and the point A, because the point B is closer to the grounded point than the point A. The voltage drop (voltage variation) at the point A due to the absorption current is greater than the voltage drop at the point B due to the identical absorption current. This is detected by the voltage-detecting amplifier-voltmeter 18 and represented in gray scale in synchronism with the scanning of the beam. In this way, a potential distribution image of the interconnect pattern formed on the specimen is obtained. In this manner, according to this embodiment, the signal produced from the second probe 12 relative to the first probe 11 is once accepted into the image memory 22 in synchronism with the scanning of the beam. In this case, the potential distribution image can be displayed on the image display portion 23 while accepting the image. Alternatively, image data accepted into the image memory can be read out at arbitrary timing and displayed on the image display portion 23. Minute variations in the voltage on the specimen 14 can be detected.

In this case, the signal obtained from the second probe 12 is fed into the voltage-detecting amplifier-voltmeter 18 via the coaxial cable 19. The voltmeter 18 may also be installed in a vacuum, outside the microscope column, or in the vacuum within the microscope column. If the voltmeter is installed in a vacuum, noise intruding from the outside via the coaxial cable 19 can be reduced. As a result, only a potential distribution image can be observed by eliminating the effects of noise.

If the result is that the resistance distribution across the interconnect pattern has a break or a discontinuous or nonuniform portion, it can be identified from contrast in gray scale on the image. The obtained voltage distribution has potential information for each pixel. Accordingly, when an image is displayed, an equipotential display function (function of displaying equaipotential lines) can be selected from the voltage information and displayed.

Figure 3:
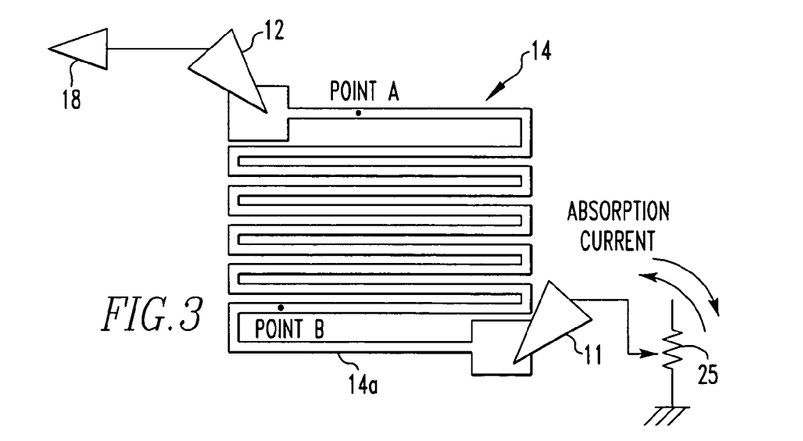
FIG. 3 is a diagram showing a second example of main portions of the present invention.

FIG. 3 shows a second example of main portions of the present invention. Like components are indicated by like reference numerals in both FIGS. 2 and 3. In this second example, the first probe 11 is grounded via a resistor. In the illustrated example, a variable resistor 25 is used as the resistor. The absorption current is shown to flow from the probe 11 toward the grounded point but the invention is not limited to this example. The current may flow from the ground potential toward the probe 11. The operation of the system constructed in this way is described below.

Where the resistance value of the interconnect pattern 14a is small and it is difficult to detect the voltage, the first probe 11 is grounded via the resistor 25. Since an absorption current flows through the resistor 25, a voltage drop occurs. That is, an offset is added to the first probe 11. Therefore, a signal is taken from the second probe 12 to which an offset is added. In this way, according to this example, an offset is added to each probe, and a potential distribution image of the specimen 14 having a low-resistance interconnect pattern can be obtained. The resistor with which the first probe 11 is connected can be either a fixed resistor or a variable resistor. If a variable resistor is used, the amount of offset can be easily optimized.

Figure 4:
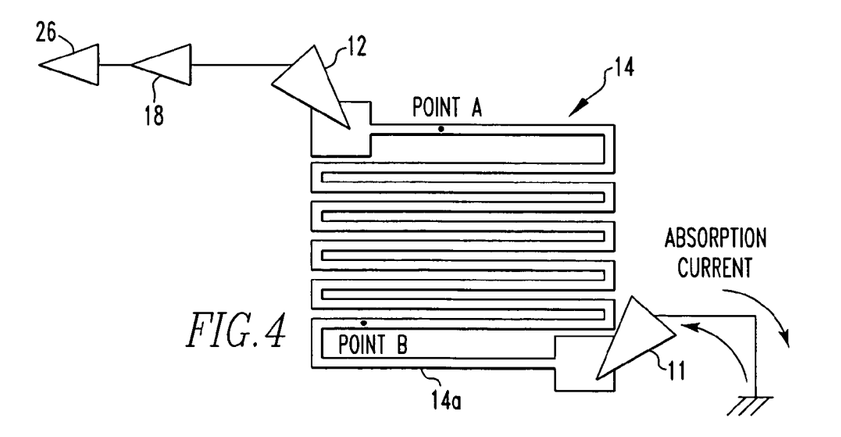
FIG. 4 is a diagram showing a third example of main portions of the present invention.

FIG. 4 shows a third example of main portions of the present invention. Like components are indicated by like reference numerals in FIGS. 2 and 4. In the illustrated example, a differentiator circuit 26 is connected to the output side of the voltage detecting amplifier-voltmeter 18. The output from the differentiator circuit 26 is displayed on the image display portion 23 (see FIG. 1). Let E be the output from the voltage detecting amplifier-voltmeter 18. Let V be the output from the differentiator circuit 26. The voltage is given by $$V=dE/dx$$

where x indicates the unit length within the interconnect pattern 14a formed on the specimen 14. The operation of the system constructed in this way is now described. The first probe 11 is grounded. The second probe 12 is contacted with the interconnect pattern 14a at the illustrated position. Under this condition, the specimen 14 is scanned with the beam of electrons or ions. As a result, secondary electrons are produced from the surface of the specimen 14 and detected by the detector 6. The output signal from the detector 6 is amplified by the amplifier 7 and then converted into digital image data by the following A/D converter 8. The computer 21 performs given image processing on the digital image data and displays an image on the image display portion 23.

Meanwhile, as the beam of electrons or ions scans over the surface of the specimen 14, an absorption current corresponding to the difference between the incident beam current and secondary electron current flows through the first probe 11. Since the absorption current flows through the interconnect pattern, the voltage signal produced at a given scan position is detected by the voltage-detecting amplifier-voltmeter 18. The detected signal representing a potential distribution image is differentiated by the subsequent differentiator circuit 26. As a result, in pattern portions where the brightness varies greatly, high differentiated values are obtained, and vice versa. Such a signal is detected in synchronism with the scanning of the beam and supplied to the image display portion 23. The image of the potential distribution across the specimen is represented in gray scale. In the obtained image, pattern portions where the potential varies greatly are emphasized. According to this example, it is possible to visually check the degree of variation at each point. In the above-described embodiment, the output from the voltage detecting amplifier-voltmeter 18 is differentiated. The present invention is not limited to this scheme. Where the amplitude of the output from the probe 12 is large, the output from the probe 12 may be differentiated.

Pattern portions giving differentiated values in excess of a given level can be displayed in colors. In this case, pattern portions where the brightness varies greatly can be visually checked more easily.

Figure 5:
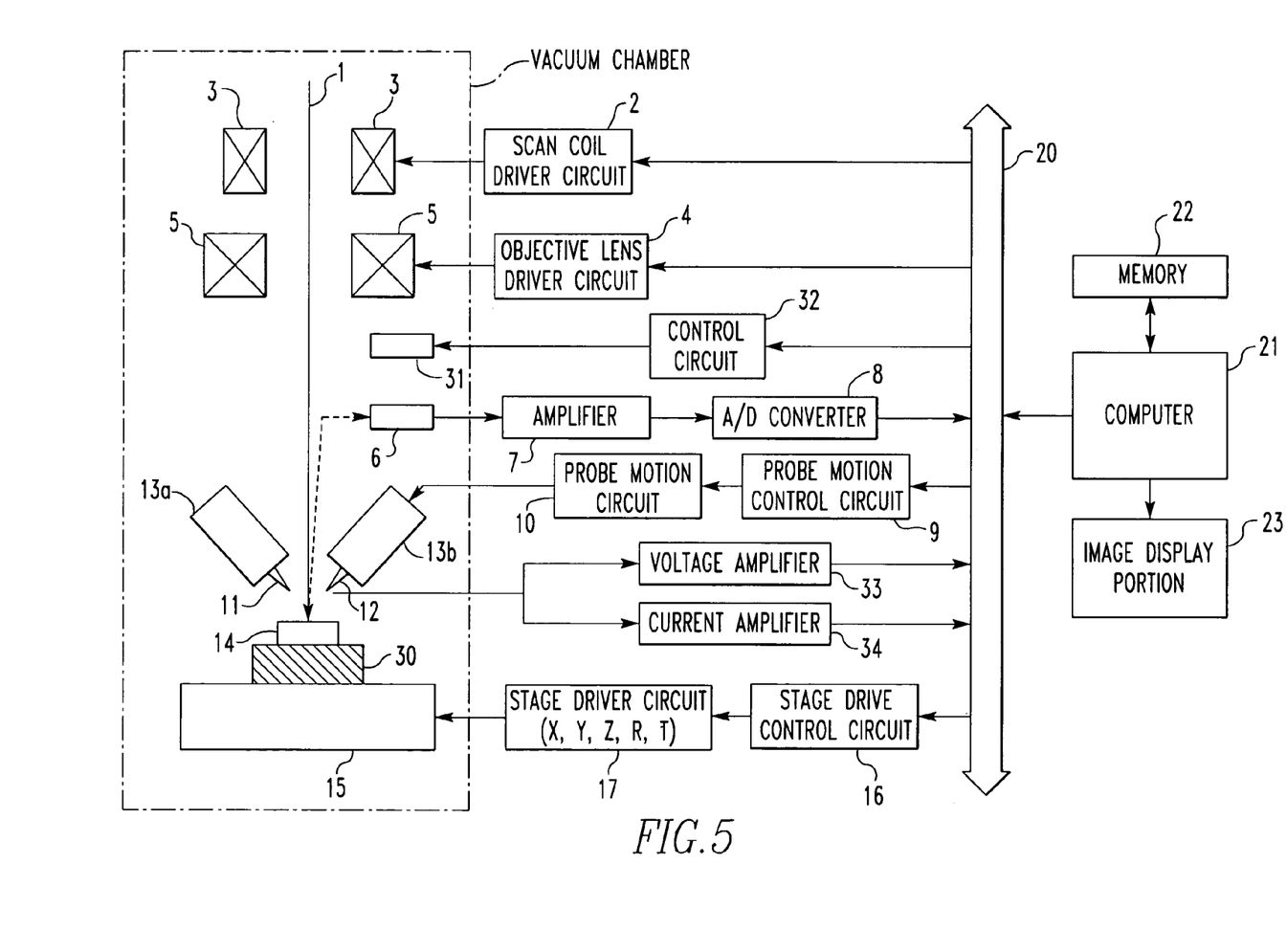
FIG. 5 is a block diagram showing a second embodiment of the present invention.

FIG. 5 shows a second embodiment of the present invention. Like components are indicated by like reference numerals in both FIGS. 1 and 5. Only those portions of FIG. 5 which are different from FIG. 1 are described. In FIG. 5, an insulating portion 30 is placed on the specimen stage 15. The specimen 14 is placed on the insulating portion 30. A deposition unit 31 marks given positions on the specimen 14 under control of a control circuit 32. The voltage signal from the second probe 12 is received by a voltage amplifier 33. The absorption current from the first probe 11 is received by a current amplifier 34. The outputs of the voltage amplifier 33 and current amplifier 34 are connected with the bus 20. The output signals from the amplifiers 33 and 34 are converted into digital image data by an A/D converter (not shown) and then supplied to the bus 20.

Figure 6:
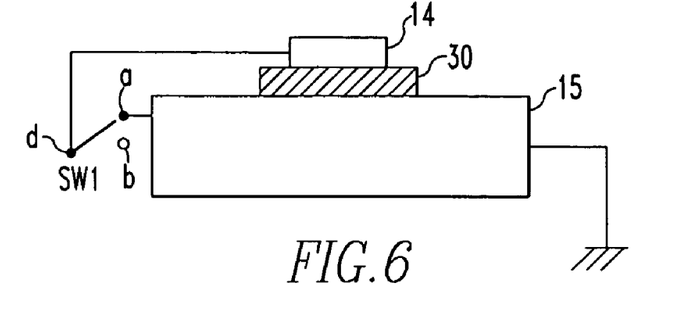
FIG. 6 is a vertical cross section of a specimen stage.

FIG. 6 shows an example of the specimen stage 15. The insulating portion 30 is formed on the stage 15. The specimen 14 is placed on the insulating portion 30. The specimen stage 15 is grounded. The specimen 14 is electrically connected with the specimen stage 15 via a switch SW1. Therefore, when the common contact d of the switch SW1 is connected with a contact a, the specimen 14 is placed at ground potential via the specimen stage 15. When the common contact d of the switch SW1 is connected with a contact b, the specimen 14 is electrically floated, i.e., insulated from the specimen stage 15. The operation of the system constructed in this way is described below.

The incident beam of electrons or ions is scanned over the specimen by the scan coils. Secondary electrons produced from each scan point on the specimen are detected by the detector 6 and then amplified by the amplifier 7. The output signal from the amplifier 7 is converted into digital image data by the following A/D converter 8 and fed into the computer 21 via the bus 20. The computer 21 displays the digital image data on the image display portion 23 and identifies pattern portions with which the probes should be contacted, based on the displayed image.

To bring the probes into contact with the pattern portions identified within the image, the probe motion control circuit 9 is controlled by the computer 21 via the bus 20. The probes 11 and 12 attached to the tips of the manipulators 13a and 13b are manipulated by the probe motion circuit 10. The probes 11 and 12 are electrically isolated from other portions and so a voltage or current can be detected. The probes 11 and 12 are contacted with certain portions of the specimen 14. The probe 11 can be connected with the voltage amplifier 33 and a grounded point switchably. Similarly, the probe 12 can be connected with the current amplifier 34 and a grounded point switchably. During approach to the contacted portion, the probes are grounded to prevent discharging; otherwise, the probes would be damaged.

Where a break in a conductor of the specimen 14 is identified, the probe 11 is connected with the current amplifier 34. Where a portion showing an abnormal resistance is identified, the probe 11 can be connected with the voltage amplifier 33. In this way, the probe can be switchingly connected. Furthermore, where plural probes are used and a potential is detected using a certain portion of a specimen as a grounded terminal, the switch SW1 is switched to the contact b. Isolation from the specimen stage 15 (at ground potential) is achieved by the insulating portion 30.

In this example, if the resistance distribution within the interconnect pattern has a discontinuous or nonuniform portion, the defective portion can be identified from the contrast in gray scale on the potential distribution image. If a conductor in the specimen pattern has a break, no absorption current is detected from this break portion of the specimen. Consequently, the break portion can be identified.

According to this embodiment, the beam of electrons or ions is scanned over the specimen. A portion with which probes are contacted is identified from the obtained image. The probes are brought into contact with the identified portion using a moving mechanism. An absorption current flowing through the probes or a voltage signal is displayed on the image display portion 23 in synchronism with the scanning of the beam. Therefore, minute variations in voltage on the specimen can be detected.

When an abnormal portion of the specimen is identified in this way, the computer 21 drives the control circuit 32 to cause the deposition unit 31 to mark certain portions on the specimen. Consequently, the position of the defective portion on the specimen can be visually observed.

Figure 7:
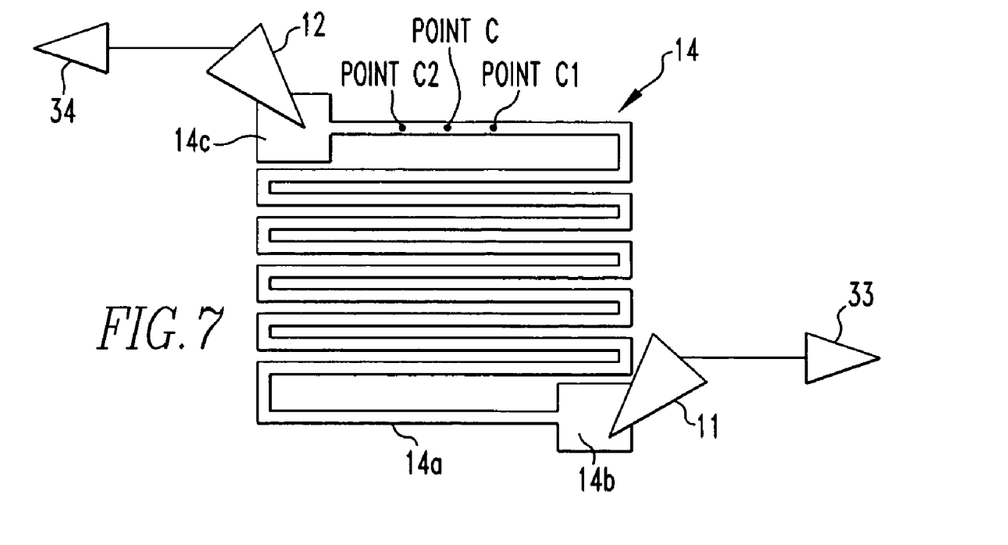
FIG. 7 is a diagram showing a modified example using the second embodiment of the present invention.

A modification of this embodiment is shown in FIG. 7. In this modified embodiment, the first probe 11 is brought into contact with a first pad 14b of the interconnect pattern 14a formed on the specimen 14, the pad 14b being in a first position. The second probe 12 is brought into contact with a second pad 14c of the interconnect pattern 14a, the pad 14c being in a second position. After the probes 11 and 12 are contacted with the pads 14b and 14c, respectively, the probes 11 and 12 are connected with the voltage amplifier 33 and current amplifier 34, respectively.

Under this condition, the beam of electrons or ions is scanned over the specimen 14. During the scanning, a voltage is detected by the voltage amplifier 33 via the probe 11. An electrical current is detected by the current amplifier 34 via the probe 12.

The output signals from the voltage amplifier 33 and current amplifier 34 which indicate the detected voltage value and current value, respectively, are sent to the computer 21 via the bus 20. The computer 21 computationally finds the resistance value of the interconnect pattern portion located between the two probes 11 and 12 over the specimen 14, based on the detected voltage value and current values. In the computation, the voltage value is divided by the current value. The quotient is the resistance value. The resistance value found by the computer 21 is displayed on the image display portion 23.

The objects with which the probes 11 and 12 are brought into contact are not limited to the pads 14b and 14c formed on the opposite ends of the interconnect pattern 14a. Arbitrary positions on the interconnect pattern 14a located between the pads 14b and 14c may be taken as first and second positions. The probes may be brought into contact with the pattern at the first and second positions.

For example, where a defective point or part, if any, of the interconnect pattern 14a is identified from an absorption current image or potential distribution image of the specimen detected when the beam is scanned over the specimen 14, the probes 11 and 12 are contacted with the interconnect pattern 14a at the first and second positions, the defective point being located between the first and second positions on the interconnect pattern 14a.

That is, where a point C on the interconnect pattern 14a shown in FIG. 7 is identified as a defective point showing a high resistance, points C1 and C2 on the opposite sides of the point C are taken as the first and second positions, respectively, on the interconnect pattern 14a. The probe 11 is brought into the point C1, while the probe 12 is brought into the point C2.

Under this condition, the resistance value is calculated from the voltage value and current value as described previously. In this way, the resistance value of the defective point C can be found more accurately.

Figure 8:
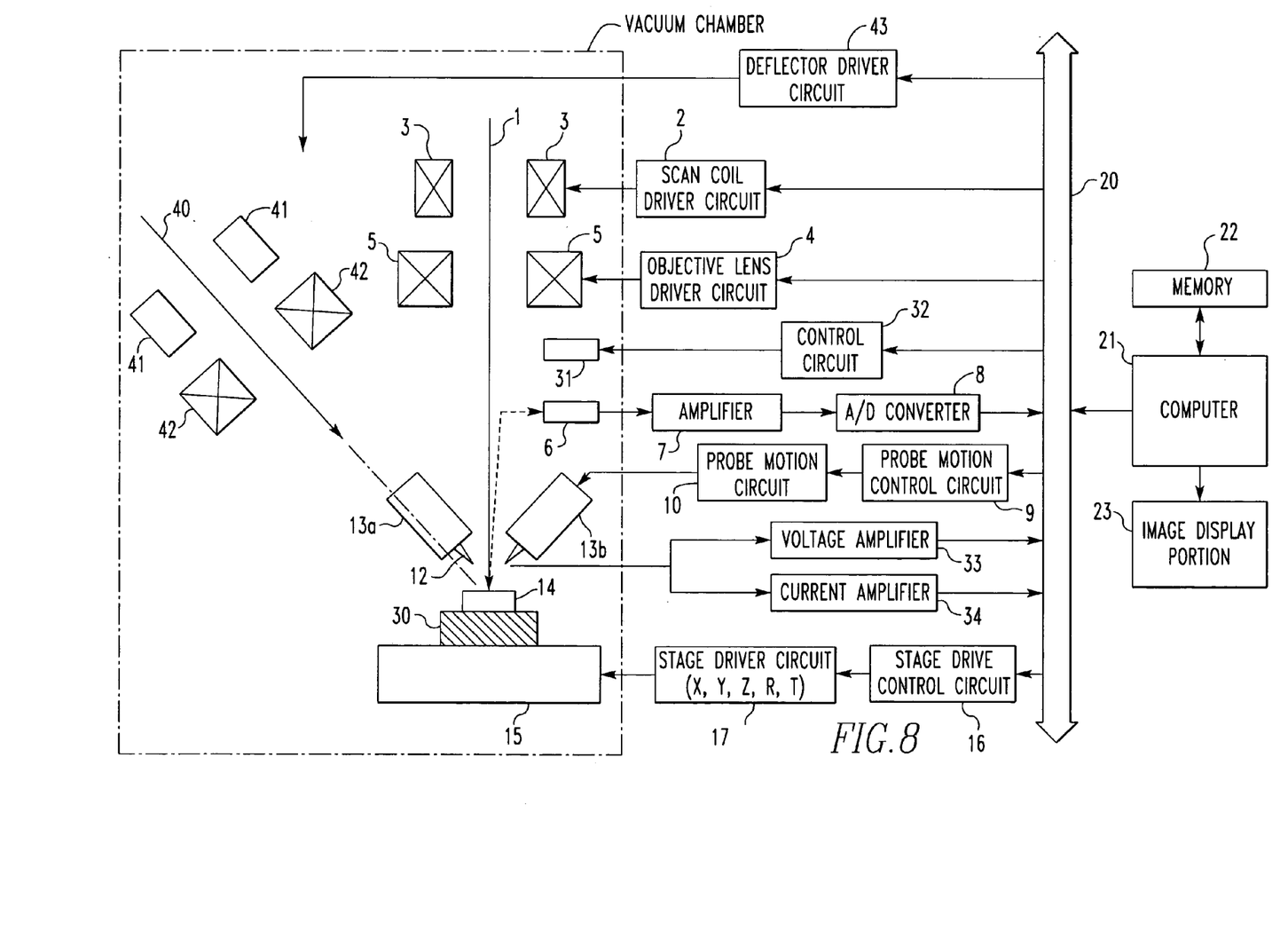
FIG. 8 is a block diagram showing a third embodiment of the present invention.

FIG. 8 shows a third embodiment of the present invention. Like components are indicated by like reference numerals in both FIGS. 5 and 8. This embodiment is characterized in that an ion beam irradiation apparatus is mounted in addition to the electron beam irradiation apparatus. The ion beam irradiation apparatus has a beam deflector 41 for deflecting an incident ion beam 40. The apparatus further includes an objective lens 42 for directing the ion beam at a specimen 14. The deflector 41 is controlled by a deflector driver circuit 43. This embodiment is identical with the embodiment of FIG. 5 in other respects. The microscope column for ion beam is so positioned that the same portion as the field of view observed with an electron beam can be observed. The operation of the system constructed in this way is described below.

A potential distribution image of the specimen 14 is obtained using the electron beam irradiation apparatus by manipulations performed in the same way as the foregoing. An abnormal portion of the specimen 14 is identified by the computer 21 from this potential distribution image. Then, the computer 21 sends a deflection control signal to the deflection driver circuit 43 via the bus 20 to cut a certain portion of the specimen 14 by the ion beam 40, thus sectioning the specimen 14.

Figure 9:
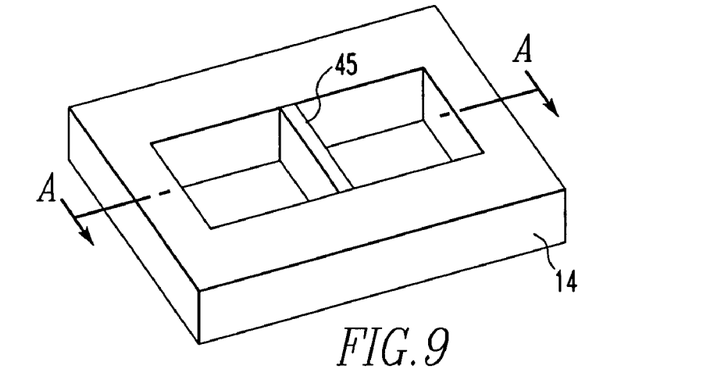
FIG. 9 is a perspective view illustrating sectioning of a specimen.
Figure 10:
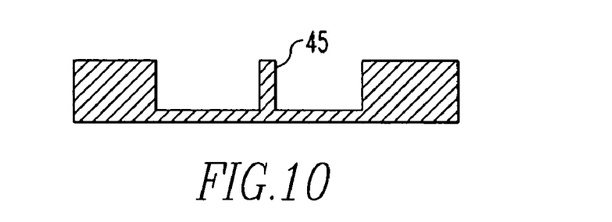
FIG. 10 is a vertical cross section taken on line A-A of FIG. 9.

FIG. 9 illustrates the sectioning of the specimen. When the certain position on the specimen 14 is irradiated and cut by the ion beam, a thin section 45, as shown in the perspective view of FIG. 9, is formed. FIG. 10 shows a cross-sectional view of this section. After sectioning the specimen 14 in this way, a cross section of the thin section 45 is irradiated by an electron beam using the electron beam irradiation apparatus. An SEM image of a cross section of the thin section 45 is obtained. The state of an abnormal portion can be recognized from the SEM image. Furthermore, if a TEM image of the thin section 45 can be obtained, the state of the abnormal portion can be recognized from the TEM image. In this way, in this embodiment, the identified defective portion is thinned by ion beam irradiation. The thinned cross section is displayed as an image by electron beam irradiation. Therefore, the state of the defective portion can be checked visually.

Furthermore, in this embodiment, a sectioned specimen can be transported to other locations using minute tweezers. Therefore, plural defective parts can be sectioned efficiently. The positions are prevented from being missed.

In the embodiment of FIG. 8, the electron-beam column is placed vertically, while the ion-beam column is tilted. The present invention is not limited to this structure. The ion-beam column may be placed vertically and the electron-beam column may be tilted.

Figure 11:
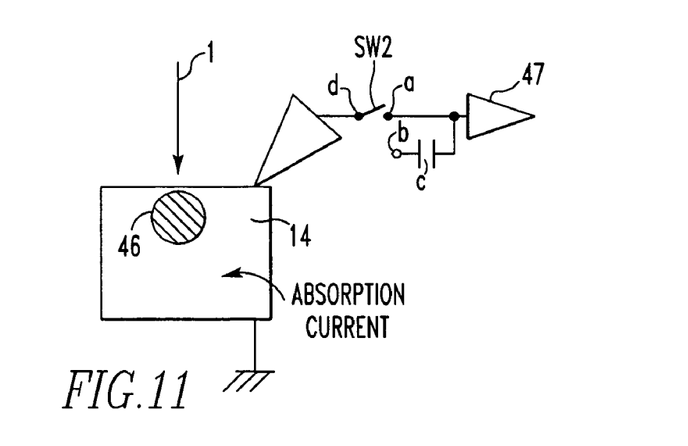
FIG. 11 is a diagram showing a fourth example of main portions of the present invention.

FIG. 11 shows a fourth example of main portions of the present invention. Like components are indicated by like reference numerals in both FIGS. 1 and 11. Indicated by reference numeral 1 is an electron beam. A specimen 14 is grounded. Indicated by numeral 46 is a foreign material. A probe 12 is contacted with the specimen 14 at a given position. A voltage signal from the probe 12 is received by a switch SW2 and then amplified by a voltage amplifier 47. When the common contact d of the switch SW2 is connected with a contact a, the signal taken from the probe 12 is directly coupled to the voltage amplifier 47. A capacitor C is connected with a contact b of the switch SW2. When the common contact d of the switch SW2 is connected with the contact b, the signal taken from the probe 12 is coupled to the voltage amplifier 47 via the capacitor C. The operation of the system constructed in this way is described below.

Where the sample 14 is grounded, the internal resistance of the specimen and the route in which the absorption current flows in vary the potential on the specimen surface. Where the electron beam 1 is directed at the foreign material 46, secondary electrons ejected from the foreign material 46 causes the sample absorption current to flow into the specimen 14. At this time, if the resistance of the foreign material 46 is large, the voltage detected by the probe 12 is large. If the absorption current is small, the voltage is small. The detected voltage signal is amplified by the voltage amplifier 47 and can be visualized. In addition, a potential distribution image unaffected by the base potential can be gained by placing the capacitor C ahead of the voltage amplifier 46 and detecting only the varying component of the signal taken from the probe 12.

Figure 12:
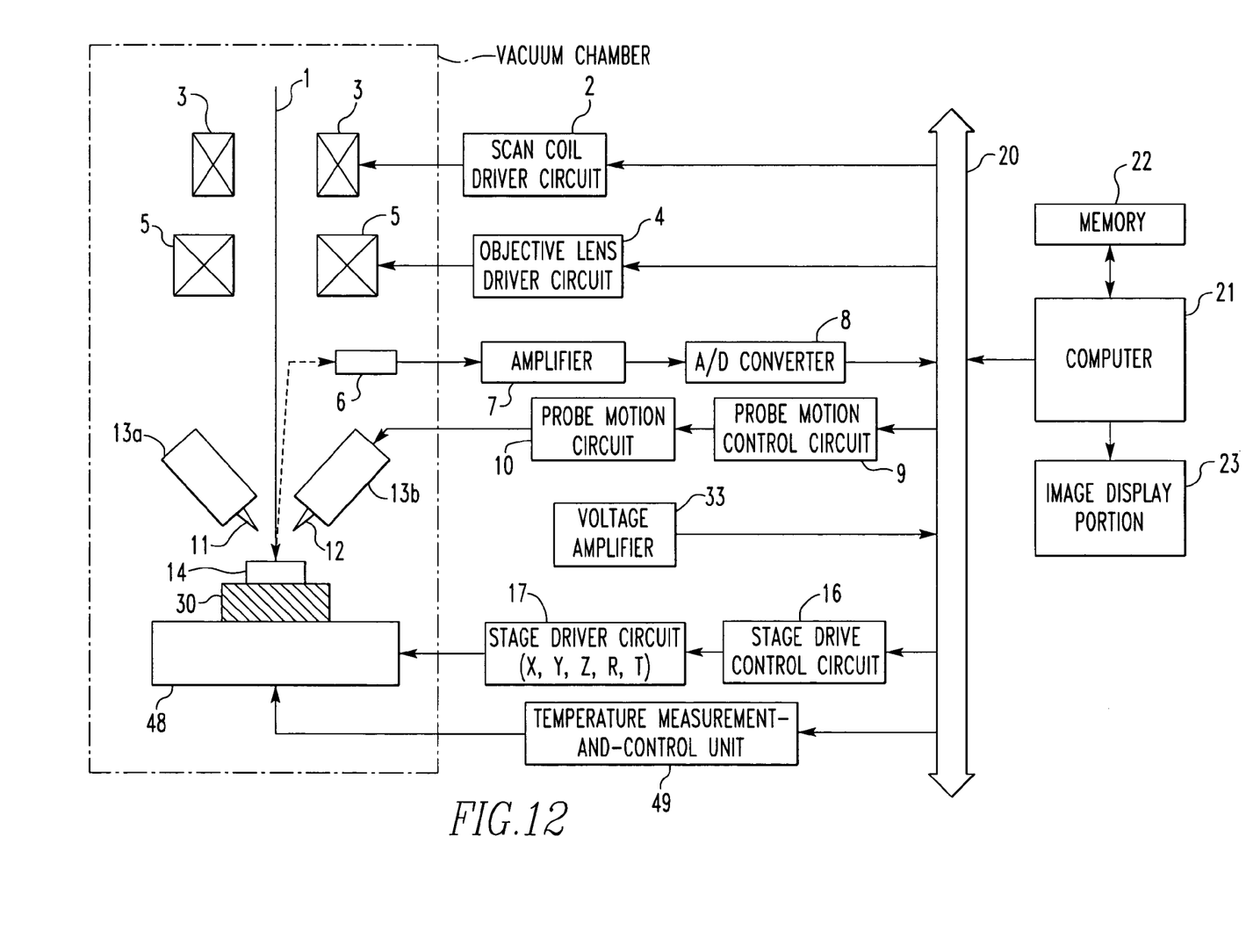
FIG. 12 is a block diagram showing a fourth embodiment of the present invention.

FIG. 12 shows a fourth embodiment of the present invention. Like components are indicated by like reference numerals in both FIGS. 5 and 12. In FIG. 12, a cooling-heating stage 48 controls the temperature of the specimen 14 constant. A temperature measurement-and-control unit 49 is connected with the cooling-heating stage 48, measures the temperature of the specimen 14, and drives the cooling-heating stage 48. The temperature measurement-and-control unit 49 is controlled by a computer 21. This fourth embodiment is identical with the embodiment illustrated in FIG. 5 in other respects. The operation of the system constructed in this way is described below.

The function of measuring and displaying a potential distribution image as shown in FIG. 12 is the same as the function of the system shown in FIG. 5. In this case, in the potential distribution-measuring apparatus, the temperature measurement-and-control unit 49 drives the cooling-heating stage 48 to vary the specimen temperature, for identifying a failure, fault, or foreign material that becomes more conspicuous as the temperature varies. In this structure, the defective portion of the specimen can be made more conspicuous by varying the specimen temperature. In consequence, a potential distribution image can be obtained at each specimen temperature.

In the embodiments described above, two probes are used. The present invention is not limited to this scheme. Three or more probes can be used. Thus, the potential distributions across plural circuits on a specimen can be detected.

The advantages of the various embodiments of the present invention described so far are recited below:

1. In a system comprising an electron microscope or ion beam apparatus, the voltage on a portion irradiated with the beam of electrons can be detected. A potential distribution across the specimen can be imaged and displayed.

2. Since the probe moving mechanism has a motion resolution of less than 10 nm, each probe can be brought into contact with a quite small area.

3. Potential distributions at plural points can be detected at the same time by installing plural probe-moving mechanisms.

4. Each probe is installed at an angle of more than 30 degrees. This facilitates approaching a specimen.

5. One end of an interconnect pattern formed on a specimen is grounded. A voltmeter is connected with the other end. Under this condition, a beam of electrons or ions is directed at the pattern along it. The voltage (potential difference with ground potential) is detected by the voltmeter. Variations in the voltage are imaged and displayed in synchronism with the scanning of the beam. In this way, a potential distribution image across the irradiated area can be gained.

6. Since amplifiers and voltmeter can be installed in a vacuum, a potential distribution image can be detected with high sensitivity and low noise.

7. Before a probe is brought into a target position, the probe is held at ground potential. After the contact, the probe is connected with the amplifiers and voltmeter. For this purpose, a sequence of operations is performed. Therefore, damage to the specimen due to discharging of the probe can be prevented.

8. By providing a function of displaying the obtained potential distribution by equipotential lines or by installing a filter, a defective portion can be identified with ease by the function of selectively displaying desired voltage ranges or voltages in desired ranges.

9. The obtained potential distribution image and secondary electron image are displayed on the viewing screen in real time. Also, a superimposing function is provided. In this manner, geometrical information about a defective portion and other information about the defective portion can be obtained simultaneously.

10. A microscope using a beam of electrons or ions is equipped with one or more probe-moving mechanisms. Potential-detecting amplifiers and absorption current-detecting amplifiers are installed. Therefore, a pattern portion showing an abnormal resistance and a break in a conductor can both be identified with a single apparatus.

11. A defective portion can be identified by a potential detection method or absorption current method using a beam of electrons or ions. The defective portion can be sectioned in the same specimen chamber by an ion beam. Hence, the throughput of the process sequence can be improved.

12. A deposition function using a beam of electrons or ions may be provided. A defective portion can be marked.

13. A sectioned specimen can be moved to other locations with minute tweezers. Therefore, plural abnormal portions can be efficiently sectioned without missing their positions.

14. It is easy to narrow down a defective portion by providing a color display of portions showing voltage variations per unit length exceeding a given level.

15. A defective portion appearing at certain temperatures can be identified by providing a specimen-cooling function.

16. A defective portion showing a different rate of change in a voltage distribution can be easily identified by differentiating a signal by a detector portion and imaging the signal.

17. A color display function is added to the viewing screen. Identification of parts can be automatically done.

In this way, in a first specimen inspection method according to the present invention, each probe is brought into a given position on a specimen. A beam of electrons or ions is scanned over the specimen. A signal taken from the probe is detected in synchronism with the scanning of the beam. Thus, a potential distribution image of the specimen is obtained. Consequently, the potential distribution image of the specimen can be gained while synchronizing the signal derived from the probe with the scanning of the beam. Minute variations in a voltage on the specimen can be detected.

In a second specimen inspection method according to the present invention, each probe is brought into a given position on a specimen. A beam of electrons or ions is scanned over the specimen. An absorption current flowing through the probe or a voltage developed on the probe during the scanning of the beam is detected as a signal. A potential distribution image of the specimen is gained while synchronizing a signal detected via the probe with the scanning of the beam. In consequence, the potential distribution image of the specimen is created while synchronizing the signal indicative of the absorption current flowing through the probe or the voltage on the probe with the scanning of the beam. Hence, minute variations in voltage on the specimen can be detected.

In a third specimen inspection method according to the present invention, one end of an interconnect pattern formed on a specimen is grounded. A voltage detector is connected via a probe to the other end of the pattern. An image is obtained by synchronizing a signal detected by the voltage detector with scanning of a beam of electrons or ions when the beam is scanned over the specimen. The obtained image is superimposed on a secondary electron image or backscattered electron image obtained by the scanning of the beam. Consequently, the position of an abnormal portion on the specimen can be identified by superimposing an image obtained by synchronizing a voltage signal derived from an interconnect pattern formed on the specimen with the scanning of the beam on a secondary electron image or backscattered electron image of the specimen.

In a fourth specimen inspection method according to the present invention, first and second probes are brought into first and second positions, respectively, on an interconnect pattern on a specimen. A beam of electrons or ions is scanned over the specimen. A voltage produced during the scanning of the beam is detected via one of the probes. An electrical current produced during the scanning of the beam is detected via the other probe. The resistance value of the interconnect pattern portion located between the probes on the specimen is obtained based on the detected voltage and current. Consequently, the voltage developed during the scanning of the beam is detected via one probe. The current produced during the scanning of the beam is detected via the other probe. Based on the detected voltage and current, the resistance value of the interconnect pattern portion located between the probes on the specimen is obtained. Therefore, the resistance value of the interconnect pattern portion can be easily detected.

A first specimen inspection system according to the present invention comprises a probe contacted with a surface of a specimen, scanning means for scanning the beam of electrons or ions over the specimen, potential detection means for detecting a potential produced on the specimen via the probe, and image acquisition means for gaining a potential distribution image of the specimen while synchronizing the output from the potential detection means with the scanning of the beam. Consequently, a potential distribution image of the specimen can be obtained while synchronizing a signal which indicates a potential on the specimen and is obtained via the probe with the scanning of the beam. Minute variations in voltage on the specimen can be detected.

A second specimen inspection system according to the present invention comprises a probe contacted with a surface of a specimen, scanning means for scanning a beam of electron or ions over the specimen, detection means for detecting an absorption current flowing through the specimen or a voltage on the specimen via the probe, and image acquisition means for gaining an image while synchronizing the detected signal with the scanning of the beam. Therefore, an image is gained in such a way that the signal indicative of the absorption current or voltage on the specimen obtained via the probe is synchronized with the scanning of the beam. Consequently, minute variations in voltage on the specimen can be detected.

A third specimen inspection system according to the present invention comprises first and second probes contacted with a specimen, scanning means for scanning a beam of electrons or ions over the specimen, voltage detection means for detecting a voltage produced during the scanning of the beam via one of the probes, current detection means for detecting an electrical current produced during the scanning of the beam via the other probe, and resistance value acquisition means for gaining a resistance value based on the detected voltage and current. The resistance value of the interconnect pattern portion can be easily detected because the voltage produced during the scanning of the beam is detected via one probe and the current produced during the scanning of the beam is detected via the other probe and because the resistance value of the interconnect pattern portion located between the probes on the specimen is gained based on the detected voltage and current.

Have thus described our invention with the detail and particularity required by the Patent Laws, what is desired protected by Letters Patent is set forth in the following claims.

The invention claimed is:

1. A specimen inspection method comprising the steps of:
   bringing a probe into contact with a specimen at a given position;
   scanning a beam of electrons or ions over the specimen; and
   detecting a voltage signal taken from the probe, which is in contact with the specimen, in synchronism with the scanning of the beam, amplifying the detected voltage signal, thus obtaining a potential distribution image of the specimen, the image being represented in gray scale by display of the amplified voltage signal in synchronism with the scanning of the beam.

2. A specimen inspection method comprising the steps of:
   bringing a probe into contact with a specimen at a given position;
   scanning a beam of electrons or ions over the specimen; and
   obtaining a potential distribution image of the specimen, the image being represented in gray scale while amplifying a voltage developed on the specimen and detected via the probe which is in contact with the specimen when the beam is scanned over the specimen with the scanning of the beam.

3. A specimen inspection method as set forth in claim 1, wherein a defective portion of the specimen, if any, is identified based on information obtained from said potential distribution image of the specimen, and wherein the defective portion is marked by driving a deposition control unit.

4. A specimen inspection method as set forth in claim 3, wherein the defective portion of the specimen is identified based on the information obtained from said potential distribution image of the specimen, the identified defective portion is irradiated with an ion beam to section the defective portion, and a cross-sectional image of the sectioned defective portion is gained by electron beam irradiation.

5. A specimen inspection method comprising the steps of:
   grounding one end of an interconnect pattern formed on a specimen;
   connecting a voltage detector with the other end of said interconnect pattern via a probe;
   scanning a beam of electrons or ions over the specimen, detecting a voltage signal produced at this time by the voltage detector via the probe which is in contact with the specimen, amplifying the detected voltage signal, synchronizing the amplified signal with the scanning of the beam, and obtaining an image, the image being represented in gray scale by display of the amplified voltage signal in synchronism with the scanning of the beam; and
   superimposing the obtained image on a secondary electron image or backscattered electron image obtained by the scanning of the beam.

6. A specimen inspection method as set forth in claim 5, wherein said one end of the interconnect pattern is grounded via a resistor.

7. A specimen inspection method as set forth in claim 1, wherein the signal detected via said probe is amplified by an amplifier installed in a vacuum chamber where said specimen is placed.

8. A specimen inspection method as set forth in claim 2, wherein the signal detected via said probe is amplified by an amplifier installed in a vacuum chamber where said specimen is placed.

9. A specimen inspection method as set forth in claim 5, wherein the signal detected via said probe is amplified by an amplifier installed in a vacuum chamber where said specimen is placed.

10. A specimen inspection method as set forth in claim 7, wherein the signal amplified by said amplifier is differentiated by a differentiator circuit installed on an output side of said amplifier, and wherein the image is obtained based on the differentiated signal.

11. A specimen inspection method as set forth in claim 8, wherein the signal amplified by said amplifier is differentiated by a differentiator circuit installed on an output side of said amplifier, and wherein the image is obtained based on the differentiated signal.

12. A specimen inspection method as set forth in claim 9, wherein the signal amplified by said amplifier is differentiated by a differentiator circuit installed on an output side of said amplifier, and wherein the image is obtained based on the differentiated signal.

13. A specimen inspection method as set forth in claim 10, wherein regions of the image which are indicated by an output signal from said differentiator circuit and which produce variations in the output signal from the differentiator circuit in excess of a given level are displayed in colors.

14. A specimen inspection method as set forth in claim 1, wherein temperature of said specimen is made adjustable, and wherein an image corresponding to the temperature of the specimen can be obtained.

15. A specimen inspection method as set forth in claim 2, wherein temperature of said specimen is made adjustable, and wherein an image corresponding to the temperature of the specimen can be obtained.

16. A specimen inspection method as set forth in claim 5, wherein temperature of said specimen is made adjustable, and wherein an image corresponding to the temperature of the specimen can be obtained.

17. A specimen inspection system comprising:
a probe to be contacted with a surface of a specimen;
scanning means for scanning a beam of electrons or ions over the specimen;
potential detection means for detecting an electric potential on said specimen via said probe which is in contact with the specimen;
amplifying means for amplifying the detected electric potential signal; and
image acquisition means for obtaining a potential distribution image of the specimen, the image being represented in gray scale by display of the amplified signal, in synchronism with the scanning of the beam, while synchronizing an output from said amplifying means and the scanning of the beam.

18. A specimen inspection system comprising:
a probe to be contacted with a surface of a specimen;
scanning means for scanning a beam of electrons or ions over the specimen;
detection means for detecting a voltage developed on the specimen via said probe which is in contact with the specimen;
amplifying means for amplifying the detected voltage signal; and
image acquisition means for obtaining an image represented in gray scale by displaying the amplified voltage signal in synchronism with the scanning of the beam.

19. A specimen inspection system as set forth in claim 17, wherein a defective portion, if any, of the specimen is identified based on information obtained from the image obtained by said image acquisition means, the identified defective portion is irradiated with an ion beam to section the defective portion, and a cross-sectional image of the sectioned defective portion is gained by electron beam irradiation.

20. A specimen inspection system as set forth in claim 18, wherein a defective portion, if any, of the specimen is identified based on information obtained from the image obtained by said image acquisition means, the identified defective portion is irradiated with an ion beam to section the defective portion, and a cross-sectional image of the sectioned defective portion is gained by electron beam irradiation.

21. A specimen inspection method comprising the steps of:
bringing first and second probes into contact with a surface of an interconnect pattern on a specimen at first and second positions, respectively;
scanning a beam of electrons or ions over the specimen;
detecting a voltage signal produced during the scanning of the beam via one of said probes both of which are in contact with the specimen and detecting an electrical current signal produced during the scanning of the beam via the other of said probes;
amplifying the detected voltage signal and the electrical current signal; and
obtaining a resistance value of an interconnect pattern portion on the specimen located between said probes, based on the amplified voltage and current signals.

22. A specimen inspection system comprising:
first and second probes to be contacted with a specimen;
scanning means for scanning a beam of electrons or ions over the specimen;
voltage detection means for detecting a voltage produced during the scanning of the beam via one of said probes both of which are in contact with the specimen;
current detection means for detecting an electrical current produced during the scanning of the beam via the other of said probes;
first amplifying means for amplifying the detected voltage signal;
second amplifying means for amplifying the detected electric current signal; and
resistance value acquisition means for obtaining a resistance value based on the amplified voltage and current signals.

* * * * *